(12) United States Patent
Tietze et al.

(10) Patent No.: US 8,853,302 B2
(45) Date of Patent: Oct. 7, 2014

(54) LIQUID MONOBENZOXAZINE BASED RESIN SYSTEM

(75) Inventors: Roger Tietze, The Woodlands, TX (US); Yen-Loan Nguyen, Spring, TX (US); Mark Bryant, The Woodlands, TX (US)

(73) Assignee: Huntsman Advanced Materials Americas LLC, The Woodlands, TX (US)

( * ) Notice: Subject to any disclaimer, the term of this patent is extended or adjusted under 35 U.S.C. 154(b) by 252 days.

(21) Appl. No.: 13/266,476

(22) PCT Filed: May 14, 2010

(86) PCT No.: PCT/US2010/034900
§ 371 (c)(1),
(2), (4) Date: Oct. 27, 2011

(87) PCT Pub. No.: WO2010/132772
PCT Pub. Date: Nov. 18, 2010

(65) Prior Publication Data
US 2012/0046388 A1     Feb. 23, 2012

Related U.S. Application Data

(60) Provisional application No. 61/178,188, filed on May 14, 2009.

(51) Int. Cl.
| | |
|---|---|
| *C08L 79/00* | (2006.01) |
| *C08L 63/00* | (2006.01) |
| *C08G 73/00* | (2006.01) |
| *C08G 59/00* | (2006.01) |
| *B29C 45/14* | (2006.01) |
| *C08G 59/40* | (2006.01) |
| *C08G 59/24* | (2006.01) |
| *C08J 5/04* | (2006.01) |
| *C07D 265/16* | (2006.01) |
| *C08K 7/02* | (2006.01) |

(52) U.S. Cl.
CPC ........... *C07D 265/16* (2013.01); *C08J 2379/04* (2013.01); *C08G 59/4014* (2013.01); *C08G 59/24* (2013.01); *C08J 5/04* (2013.01); *C08K 7/02* (2013.01); *C08J 2363/00* (2013.01)
USPC ............... 523/400; 528/87; 528/97; 528/421; 528/423; 524/99; 524/110; 264/257

(58) Field of Classification Search
CPC ......... C08L 63/00; C08L 79/00; C08G 73/00; C08G 59/00; C08G 59/24; B29C 45/44
USPC .................... 523/400; 528/393, 421; 264/257
See application file for complete search history.

(56) References Cited

U.S. PATENT DOCUMENTS

| | | | |
|---|---|---|---|
| 4,607,091 A | * | 8/1986 | Schreiber ....................... 528/96 |
| 5,021,484 A | | 6/1991 | Schreiber et al. |
| 6,743,852 B2 | | 6/2004 | Dershem et al. |

FOREIGN PATENT DOCUMENTS

WO     00/61650     10/2000

OTHER PUBLICATIONS

International Search Report regarding corresponding application No. PCT/US2010/034900, dated Sep. 8, 2010.

* cited by examiner

*Primary Examiner* — Randy Gulakowski
*Assistant Examiner* — Ha Nguyen

(57) ABSTRACT

The present invention provides a liquid resin system including a liquid monobenzoxazine monomer and a non-glycidyl epoxy compound, wherein the weight ratio of the monobenzoxazine monomer to the non-glycidyl epoxy compound is in a range of about 25:75 to about 60:40. The liquid resin system exhibits a low viscosity and exceptional stability over an extended period of time making its use in a variety of composite manufacturing methods highly advantageous.

16 Claims, No Drawings

LIQUID MONOBENZOXAZINE BASED RESIN SYSTEM

CROSS-REFERENCE TO RELATED APPLICATION

This application is the National Phase of International Application PCT/US2010/034900 filed May 14, 2010 which designated the U.S. and which claims priority to U.S. patent application Ser. No. 61/178,188 filed May 14, 2009. The noted applications are incorporated herein by reference.

STATEMENT REGARDING FEDERALLY SPONSORED RESEARCH OR DEVELOPMENT

The invention was made with U.S. Government support under Contract No. DE-FG36-07G017012 awarded by the U.S. Department of Energy. Thus, the U.S. Government has certain rights in the invention.

FIELD OF INVENTION

This invention relates to a highly stable, low viscosity resin system comprising a liquid monobenzoxazine resin and at least one non-glycidyl epoxy compound. This resin system, when used alone or in combination with other components, may be useful as a resin transfer molding resin, vacuum assisted resin transfer molding resin, pultrusion resin, adhesive, prepreg resin, or in other composite manufacturing type applications.

BACKGROUND OF THE INVENTION

Fiber reinforced polymeric matrix composites are being used in many structural applications such as aircraft, aerospace, automotive, and sporting goods applications. Generally, these high performance composites contain orientated continuous carbon fibers cured in a matrix resin. Glass or Kevlar® fibers may also be used in these applications. While there are many types of matrices that find use in composite applications, epoxy resins have dominated the market due to ease of use, excellent properties, and relatively low cost.

More recently, because of their excellent physical and mechanical properties and high thermal stability, polybenzoxazine resins have been used in producing high performance composites. Such polybenzoxazine resins can be obtained from the reaction of polyhydric phenols, formaldehyde and an amine as described in U.S. Pat. Nos. 4,607,091, 5,152,993, 5,266,695 and 5,543,516. One drawback to such polybenzoxazine resins is they are solid at room temperature and must be melted when used in the manufacture of composites, for example, in resin transfer molding (RTM) and vacuum assisted resin transfer molding (VaRTM) manufacturing processes.

In RTM and VaRTM, a fiber preform is fabricated in the shape of a finished composite article then placed in a closed cavity mold. A resin is then injected into the mold to initially wet and eventually impregnate the preform. In RTM, the resin is injected under pressure into the mold and then cured to produce the composite. In VaRTM, the preform is covered by a flexible sheet or liner which is clamped onto the mold to seal the preform in an envelope. The resin is then introduced into the envelope to wet the preform and a vacuum is applied to the interior of the envelope via a vacuum line to collapse the flexible sheet against the preform and draw the resin through the preform. The resin is then cured while being subjected to vacuum.

Thus, in both RTM and VaRTM systems, the resin which is used must possess a very low injection viscosity to allow for complete wetting and impregnation of the preform. Further, the resin must maintain such low viscosity for a period of time sufficient to completely fill the mold and impregnate the fiber preform. Finally, the resin must be homogeneous before cure. These requirements limit the use of polybenzoxazine resins in RTM and VaTRM systems since, upon melting, they impart a higher than desired viscosity, contain solids in particulate form and quickly return to a solid form at temperatures below about 100° C.

WO 2000/61650 describes the preparation of a liquid benzoxazine resin from a monohydric phenol, aldehyde and amine and its use in applications where it's necessary to apply a benzoxazine resin as a liquid at room temperature. However, this liquid benzoxazine resin still exhibits a higher than desired viscosity at room temperature and a short pot life making its use in RTM and VaRTM systems challenging.

SUMMARY OF THE INVENTION

The present invention provides a liquid resin system containing:

(a) a liquid monobenzoxazine monomer of the formula (I)

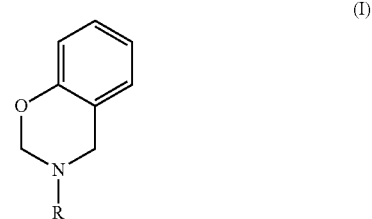

wherein R is an aliphatic or aromatic group; and (b) at least one non-glycidyl epoxy compound, wherein the weight ratio of component (a) to component (b) is in a range of about 25:75 to about 60:40.

The liquid resin system exhibits a viscosity of less than 500 cps at room temperature and exceptional stability over an extended period of time thus making its use in RTM and VaRTM, as well as other composite manufacturing methods, highly advantageous.

According to another embodiment, the present invention relates to a process for producing a composite article in a resin transfer molding system. The process includes the steps of: a) providing a fiber preform in a mold; b) injecting the liquid resin system of the present invention into the mold, c) allowing the liquid resin system to impregnate the fiber preform; and d) heating the resin impregnated preform at a temperature of at least about 90° C. for a sufficient period of time to produce an at least partially cured solid article. The partially cured solid article may then be subjected to post curing operations to produce the final composite article.

In an alternative embodiment, the present invention relates to a process for forming a composite article in a vacuum assisted resin transfer molding system. The process includes the steps of a) providing a fiber preform in a mold; b) injecting the liquid resin system of the present invention into the mold; c) reducing the pressure within the mold; d) maintaining the mold at about the reduced pressure; e) allowing the matrix resin to impregnate the fiber preform; and f) heating the resin impregnated preform at a temperature of at least about 90° C. for sufficient time to produce an at least partially cured solid article. The partially cured solid article may then be subjected to post curing operations to produce the final composite article.

DETAILED DESCRIPTION OF THE INVENTION

In general, the present invention provides a liquid resin system containing: (a) a liquid monobenzoxazine monomer; and (b) at least one non-glycidyl epoxy compound, wherein the weight ratio of the liquid monobenzoxazine monomer (a) to non-glycidyl epoxy resin (b) is in a range of about 25:75 to about 60:40. It has been surprisingly found that the liquid resin system, when formulated in such a manner, exhibits a viscosity of less than 500 cps at room temperature thus making it highly suitable for use in the production of high performance composites in various composite manufacturing methods including RTM, VaRTM, pultrusion and filament processing. By "room temperature" it is meant a temperature of about 20° C.-25° C. Furthermore, it has been unexpectedly discovered that the liquid resin system exhibits exceptional stability during storage for an extended period of time. Finally, the liquid resin system, upon curing, provides a cured product having an excellent balance of mechanical and chemical properties including, for example, a high glass transition temperature ($T_g$), decomposition temperature ($T_d$), high tensile strength, low coefficient of thermal expansion, and good flexibility.

Monobenzoxazine Monomer

The liquid resin system of the present invention includes a liquid monobenzoxazine monomer. As used herein, the term "monobenzoxazine monomer" refers to a monomer having one benzoxazine group per molecule. In addition, where the term "liquid monobenzoxazine monomer" is used, it is to be understood that one or more liquid monobenzoxazine monomers may be used together.

The liquid monobenzoxazine monomer may be represented by the general formula (I)

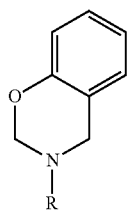

(I)

where R is an aliphatic or aromatic group. According to one embodiment, R is allyl, an unsubstituted or substituted phenyl, an unsubstituted or substituted $C_1$-$C_8$ alkyl group, or an unsubstituted or substituted $C_3$-$C_8$ cycloalkyl group. Suitable substituents on the R-group include amino, $C_1$-$C_4$ alkyl and allyl. Typically, one to four substituents may be present in the substituted R-groups. Preferably R is phenyl.

The liquid monobenzoxazine monomer may be obtained by the reaction of a monohydric phenol compound, an aldehyde and a primary amine under removal of water. The molar ratio of monohydric phenol compound to aldehyde may be from about 1:2 to about 1:2.4, preferably from about 1:2.2 to about 1:2.35, and the molar ratio of phenol compound to primary amine reactant may be from about 1:1.

The monohydric phenol compound may have from 6 to 12 carbon atoms, most preferably 6 carbon atoms, and may be substituted or unsubstituted. Preferably, a substituent, if present, is in the meta position. Examples of the monohydric phenol compound include phenol, m-and p-cresol, m-and p-ethylphenol, mand p-isopropylphenol, m-and p-methoxyphenol, m-and p-ethoxyphenol, m-and p-isopropyloxyphenol, m-and p-chlorophenol, 1-and 2-naphthol and mixtures thereof The aldehyde may have from 1 to 6 carbon atoms. Preferably, the aldehyde is formaldehyde, available either as a solution in water or as paraformaldehyde which breaks down into formaldehyde.

Examples of primary amines include: aromatic mono-or di-amines, aliphatic amines, cycloaliphatic amines and heterocyclic monoamines; for example, aniline, o-, m-and p-phenylene diamine, benzidine, 4,4'-diaminodiphenyl methane, cyclohexylamine, butylamine, methylamine, hexylamine, allylamine, furfurylamine ethylenediamine, and propylenediamine The amines may, in their respective carbon part, be substituted by $C_1$-$C_8$ alkyl or allyl. Preferred primary amines are according to the general formula $R_aNH_2$, where $R_a$ is allyl, unsubstituted or substituted phenyl, unsubstituted or substituted $C_1$-$C_8$ alkyl or unsubstituted or substituted $C_3$-$C_8$ cycloalkyl. Suitable substituents on the $R_a$ group include amino, $C_1$-$C_4$ alkyl and allyl. Typically, one to four substituents may be present on the substituted $R_a$ groups. Preferably $R_a$ is phenyl. The reaction time can vary widely with reactant concentration, reactivity and temperature. For example, reaction times may vary from a few minutes for solventless reactions to a few hours, for example 2 hours to 10 hours, for diluted reactions. If a water based solution of formaldehyde is used as the aldehyde, then a water miscible organic solvent may be used. If one or more reactant is a liquid, it may be used to dissolve the other reactant(s). If all of the reactants are solid, they may be first premixed and then melted or first melted and then premixed. The temperature of the reaction may be determined by routine experimentation by noting the formation of monobenzoxazine and less desired products and then optimizing temperature and time for the desirable product. According to one embodiment, the reaction temperature may range from about 0° C.-250° C., preferably from about 50° C.-150° C., and more preferably from about 80° C.-120° C. The monobenzoxazine synthesis reaction may be conducted at atmospheric pressure or at pressures up to about 100 psi. According to another embodiment, the reaction is carried out in the presence of an organic solvent. The organic solvent may be an aromatic solvent, for example toluene or xylene, dioxane, a ketone, for example methylisobutylketone, or an alcohol, for example isopropanol, sec-butanol or amyl alcohol. The organic solvent may also be a mixture of organic solvents.

Non-Glycidyl Epoxy Compound

The liquid resin system of the present invention also includes at least one non-glycidyl epoxy compound. The non-glycidyl epoxy compound may be linear, branched, or cyclic in structure. For example, there may be included one or more epoxy compounds in which the epoxide groups form part of an alicyclic or heterocyclic ring system. Others include an epoxy-containing compound with at least one epoxycyclohexyl group that is bonded directly or indirectly to a group containing at least one silicon atom. Examples are disclosed in U.S. Pat. No. 5,639,413, which is incorporated herein by reference. Still others include epoxy compounds which contain one or more cyclohexene oxide groups and epoxies which contain one or more cyclopentene oxide groups.

Particularly suitable non-glycidyl epoxy compounds include the following difunctional non-glycidyl epoxide compounds in which the epoxide groups form part of an alicyclic or heterocyclic ring system: bis(2,3-epoxycyclopentyl) ether, 1,2-bis(2,3-epoxycyclopentyloxy)ethane,3'',4''-epoxycyclohexyl-methyl-3,4-epoxycyclohexanecarboxylate, bis(3,4-epoxycylohexylmethyl) adipate, 3,4-epoxy-6-methyl-cyclohexylmethyl 3,4-epoxy-6-methylcyclohexanecarboxylate, di(3,4-epoxycyclohexylmethyl)hexanedioate, di(3,4-epoxy-6-methylcyclohexylmethyl) hexanedioate, ethylenebis(3,4-epoxycyclohexanecarboxylate), ethanediol di(3,4-epoxycyclohexylmethyl)ether, vinylcyclohexene dioxide, dicyclopentadiene diepoxide or 2-(3,4-epoxycyclohexyl-5,5-spiro-3,4-epoxy)cyclohexane-1,3-dioxane, and 2,2'-bis -(3,4-epoxy-cyclohexyl)-propane.

According to another embodiment, the non-glycidyl epoxy compound is a cycloaliphatic epoxy compound selected from 3',4'-epoxycyclohexyl-methyl-3,4-epoxycyclohexanecarboxylate, 3,4-epoxycyclohexyloxirane, 2-(3',4'-epoxycyclohexyl)-5,1''-spiro-3'',4''-epoxycyclohexane-1,3-dioxane, vinyl cyclohexene monoxide, 3,4-epoxycyclohexanecarboxylate methyl ester and bis(3,4-epoxycyclohexylmethyl) adipate.

The liquid resin system of the present invention can be prepared in known manner, for example, by mixing the components together using customary devices, such as a stirred vessel, stirring rod, ball mill, sample mixer, static mixer or ribbon blender. In one embodiment, the liquid resin system is formulated in such a manner that the weight ratio of the liquid monobenzoxazine monomer to the non-glycidyl epoxy resin is about 25:75 to about 60:40. In another embodiment, the liquid resin system is formulated so that the weight ratio of the liquid monobenzoxazine monomer to the non-glycidyl epoxy resin is about 35:65 to about 57:43. In another embodiment, the liquid resin system is formulated so that the weight ratio of the liquid monobenzoxazine monomer to the non-glycidyl epoxy resin is about 45:55 to about 55:45. In yet another embodiment, the liquid resin system is formulated so that the weight ratio of the liquid monobenzoxazine monomer to the non-glycidyl epoxy resin is about 50:50. Once formulated, the liquid resin system can be packaged in a variety of containers such as steel, tin, aluminium, plastic, glass or cardboard containers.

By thermally curing the liquid resin system of the present invention at temperatures above 90° C., preferably at a temperature from about 90° C. to about 200° C., inflammable polymeric resins may be obtained. Thus, according to another embodiment, the liquid resin system of the present invention may be used by itself or as part of a thermosetting resin matrix in preparing flame retarded castings, prepregs, laminates or infusion systems. As used herein, "flame retarded" means meeting the UL 94 standard criterion V0.

In one embodiment, the liquid resin system of the present invention is used as part of a thermosetting resin matrix. The thermosetting resin matrix may contain at least about 30% by weight, based on the total weight of the thermosetting resin matrix, of the liquid resin system of the present invention. In another embodiment, the thermosetting resin matrix may contain at least about 50% by weight, based on the total weight of the thermosetting resin mixture, of the liquid resin system of the present invention. In still another embodiment, the thermosetting resin matrix may contain at least 70% by weight, based on the total weight of the thermosetting resin mixture, of the liquid resin system of the present invention. In addition, the thermosetting resin matrix may contain at least one of a solvent, a catalyst, a flame retardant and/or fillers.

Examples of solvents useful in the thermosetting resin matrix include methylethylketone, acetone, N-methyl-2-pyrrolidone, N,N-dimethyl formamide, pentanol, butanol, dioxolane, isopropanol, methoxy propanol, methoxy propanol acetate, dimethylformamide, glycols, glycol acetates, toluene and xylene and mixtures thereof. The thermosetting resin matrix may include from about 5%-30% by weight, based on the total weight of the thermosetting resin matrix, of the solvent.

Examples of catalysts useful in the thermosetting resin matrix include thiodipropionic acid, phenols, thiodiphenol benzoxazine, sulfonyl benzoxazine, sulfonyl and diphenol. The thermosetting resin matrix may include from about 0.001%-2% by weight, based on the total weight of the thermosetting resin matrix, of the catalyst.

Examples of flame retardants useful in the thermosetting resin matrix include phosphorus flame retardants such as DOPO (9,10-dihydro-9-oxa-phosphaphenanthrene-10-oxide), Fyroflex® PMP flame retardant (a reactive organophosphorus additive modified with hydroxyl groups at its chain ends), CN2645A (a material based on phosphine oxide and containing phenolic functionality available from Great Lakes Chemical Corp.), Exolit flame retardants (available from Clariant), brominated polyphenylene oxide and ferrocene. The thermosetting resin matrix may include from about 0.1%-50% by weight, based on the total weight of the thermosetting resin matrix, of the flame retardant.

Examples of fillers useful in the thermosetting resin matrix include ammonium polyphosphates, plasticizers, inorganic and organic phosphorus containing compounds, micro hollow spheres and metal powders. The thermosetting resin matrix may include from about 0.001%-10% by weight, based on the total weight of the thermosetting resin matrix, of fillers.

The thermosetting resin matrix can be prepared in known manner, for example, by premixing individual components and then mixing these premixes, or by mixing all of the components together using customary devices.

As described above, the liquid resin system or thermosetting resin matrix, once formulated, may be applied to a substrate and cured at a temperature of at least 90° C. to form a flame retarded composite article. Besides RTM and VaRTM systems, the liquid resin system and thermosetting resin matrix may be used in other methods and systems for producing flame retarded composite articles including hot-pressing of prepregs, sheet molding compound, molding, casting, pultrusion and filament winding.

The properties of the flame retarded composite articles can be tailored for certain applications by the addition of reinforcement fibers. Examples of reinforcement fibers include glass, quartz, carbon, alumina, ceramic, metallic, aramid, natural fibers (e.g. flax, jute, sisal, hemp), paper, acrylic and polyethylene fibers and mixtures thereof. The reinforcement fibers may be in any of various modes, for example, as a strand or roving formed by paralleling continuous fibers or discontinuous fibers (short fibers) in one direction, cloth such as woven fabric or mat, braids, unidirectional, bi-directional, random, pseudo-isotropic or three-dimensionally dispersed mat-like material, heterogeneous lattice or mesh material, and three-dimensional material such as triaxially woven fabric.

Thus, according to another embodiment, there is provided a method for producing a flame retarded composite article in a resin transfer molding system. The process includes the steps of: a) introducing a fiber preform comprising reinforcement fibers into a mold; b) injecting the liquid resin system of the present invention into the mold, c) allowing the liquid resin system to impregnate the fiber preform; and d) heating the resin impregnated preform at a temperature of least about 90° C., preferably at least about 90° C. to about 200° C. for a sufficient period of time to produce an at least partially cured solid article; and e) optionally subjecting the partially cured solid article to post curing operations to produce the flame retarded composite article.

In another embodiment, there is provided a method for producing a flame retarded composite article in a resin transfer molding system. The process includes the steps of: a) introducing a fiber preform comprising reinforcement fibers into a mold; b) injecting a thermosetting resin matrix comprising the liquid resin system of the present invention into the mold, c) allowing the thermosetting resin matrix to impregnate the fiber preform; and d) heating the resin impregnated preform at a temperature of least about 90° C., preferably at least about 90° C. to about 200° C. for a sufficient period of time to produce an at least partially cured solid article; and e) optionally subjecting the partially cured solid article to post curing operations to produce the flame retarded composite article.

In an alternative embodiment, the present invention provides a method for forming a flame retarded composite article in a vacuum assisted resin transfer molding system. The process includes the steps of a) introducing a fiber preform comprising reinforcement fibers into a mold; b) injecting the liquid resin system of the present invention into the mold; c) reducing the pressure within the mold; d) maintaining the mold at about the reduced pressure; e) allowing the liquid resin system to impregnate the fiber preform; and f) heating the resin impregnated preform at a temperature of at least about 90° C., preferably at least about 90° C. to about 200° C. for a sufficient period of time to produce an at least partially cured solid article; and e) optionally subjecting the at least partially cured solid article to post curing operations to produce the flame retarded composite article.

In still another embodiment, the present invention provides a method for forming a flame retarded composite article in a vacuum assisted resin transfer molding system. The process includes the steps of a) introducing a fiber preform comprising reinforcement fibers into a mold; b) injecting a thermosetting resin matrix comprising the liquid resin system of the present invention into the mold; c) reducing the pressure within the mold; d) maintaining the mold at about the reduced pressure; e) allowing the thermosetting resin matrix to impregnate the fiber preform; and f) heating the resin impregnated preform at a temperature of at least about 90° C., preferably at least about 90° C. to about 200° C. for a sufficient period of time to produce an at least partially cured solid article; and e) optionally subjecting the at least partially cured solid article to post curing operations to produce the flame retarded composite article.

The liquid resin system or thermosetting resin matrix of the present invention is especially suitable for use in applications where high heat stabilities are required, for example, in forming a composite article for use as a fuel cell used for: supplying power in conventional automobiles, hybrid cars, small boats; small-scale local power generation; household power generation; simple power supplies for isolated facilities such as camp sites; and as power supplies for satellites, space development and computers.

Thus, in a particular embodiment, the liquid resin system or thermosetting resin matrix may be applied to graphite and molded to produce a fuel cell. The graphite, liquid resin system or thermosetting resin matrix, and an optional release agent, for example, carnauba wax, fatty acid ester, metal salts of stearic acid or montanic acid, are blended in a mixer, kneaded, and either injection molded, transfer molded or compression molded to produce the fuel cell.

In still another embodiment, the liquid resin system or thermosetting resin matrix, upon curing, provides a cured composite article having a glass transition temperature greater than 120° C., preferably greater than 160° C., most preferably greater than 200° C., and especially preferably greater than 230° C.

EXAMPLE

A liquid monobenzoxazine was prepared from the reaction of phenol, formaldehyde and aniline. Resin system 1 according to the present invention was then prepared by mixing the liquid monobenzoxazine with a cycloaliphatic epoxy resin at a weight ratio of about 45:55 to about 55:45. Resin system 1, along with a comparative resin system 2 which contained only the liquid monobenzoxazine, were then stored at room temperature for an extended period of time. The viscosity, gel time at 200° C. and onset temperature for each resin system was then measured initially and at 1 month and the results are shown below in Table 1:

TABLE 1

| Property | Resin System 1 | Comparative Resin System 2 |
|---|---|---|
| Initial viscosity at room temperature (cps) | 381 | 4500 |
| 1 month viscosity at room temperature (cps) | 434 | 115,000 |
| Initial gel time at 200° C. (sec) | 583 | 712 |
| 1 month gel time at 200° C. (sec) | 1180 | 661 |
| Initial onset temperature (° C.) | 222 | 179 |
| 1 month onset temperature (° C.) | 226 | 176 |

Resin system 1 was also cast and cured for 2 hours at 200° C. The cured product exhibited a glass transition temperature of 164° C. via DSC and 171° C. via TMA.

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:
1. A liquid resin system comprising:
(a) a liquid monobenzoxazine monomer of the formula (I)

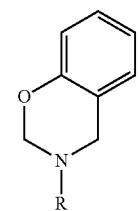

(I)

wherein R is allyl, unsubstituted or substituted phenyl, unsubstituted or substituted $C_1$-$C_8$ alkyl group, or unsubstituted or substituted $C_3$-$C_8$ cycloalkyl group; and
(b) at least one non-glycidyl epoxy compound,
wherein the weight ratio of component (a) to component (b) is in a range of about 45:55 to about 55:45 and upon curing provides a cured solid article having a glass transition temperature greater than 160° C.

2. The liquid resin system according to claim 1 wherein R is phenyl.

3. The liquid resin system according to claim 1 wherein the non-glycidyl epoxy compound is a cycloaliphatic epoxy compound.

4. The liquid resin system according to claim 3, wherein the cycloaliphatic epoxy compound is selected from 3',4'-epoxy-cyclohexyl-methyl-3,4-epoxycyclohexanecarboxylate, 3,4-epoxycyclohexyloxirane, 2-(3',4'-epoxycyclohexyl)-5,1"-spiro-3",4"-epoxycyclohexane-1,3-dioxane, vinyl cyclohexene monoxide, 3,4-epoxycyclohexanecarboxylate methyl ester and bis(3,4-epoxycyclohexylmethyl)adipate.

5. The liquid resin system according to claim 1, wherein the weight ratio of component (a) to component (b) is in a range of about 50:50.

6. The liquid resin system according to claim 1, wherein the viscosity of the liquid resin system is less than 500 cps at room temperature.

7. A method for producing a flame retarded composite article in a resin transfer molding system comprising: a) introducing a fiber preform comprising reinforcement fibers into a mold; b) injecting a thermosetting resin matrix comprising the liquid resin system according to claim 1 into the mold, c) allowing the thermosetting resin matrix to impregnate the fiber preform; and d) heating the resin impregnated preform at a temperature of at least 90° C. for a period of time to produce an at least a partially cured solid article; and e) optionally subjecting the partially cured solid article to post curing operations to produce the flame retarded composite article.

8. A method for forming a flame retarded composite article in a vacuum assisted resin transfer molding system comprising a) introducing a fiber preform comprising reinforcement fibers into a mold; b) injecting a thermosetting resin matrix comprising the liquid resin system according to claim 1 into the mold; c) reducing the pressure within the mold; d) maintaining the mold at about the reduced pressure; e) allowing the thermosetting resin matrix to impregnate the fiber preform; and f) heating the resin impregnated preform at a temperature of at least about 90° C. for a period of time to produce an at least a partially cured solid article; and e) optionally subjecting the at least partially cured solid article to post curing operations to produce the flame retarded composite article.

9. A process for preparing a flame retarded composite article comprising thermally curing a thermosetting resin mixture comprising the liquid resin system according to claim 1 at a temperature above about 90° C.

10. A flame retarded composite article prepared according to the process of claim 9.

11. A thermosetting resin matrix comprising at least 30% by weight, based on the total weight of the thermosetting resin matrix, of the liquid resin system according to claim 1 and at least one of a solvent, a catalyst, a flame retardant, and/or fillers.

12. A liquid resin system comprising:
(a) a liquid monobenzoxazine monomer obtained by the reaction of a monohydric phenol compound, an aldehyde and a primary amine wherein the molar ratio of monohydric phenol compound to aldehyde is from about 1:2.2 to about 1:2.35 and the molar ratio of monohydric phenol compound to primary amine is from about 1:1;
(b) at least one non-glycidyl epoxy compound wherein the weight ratio of component (a) to component (b) is in a range of about 45:55 to about 55:45 and upon curing provides a cured solid article having a glass transition temperature greater than 160° C.

13. The liquid resin system according to claim 12, wherein the monohydric phenol compound is phenol, m- and p-cresol, m- and p-ethylphenol, m- and p-isopropylphenol, m- and p-methoxyphenol, m- and p-ethoxyphenol, m- and p-isopropyloxyphenol, m- and p-chlorophenol, 1- and 2-naphthol or a mixture thereof.

14. The liquid resin system according to claim 13, wherein the primary amine is an amine of the formula $R_aNH_2$, wherein $R_a$ is allyl, unsubstituted or substituted phenyl, unsubstituted or substituted $C_1$-$C_8$ alkyl or unsubstituted or substituted $C_3$-$C_8$ cycloalkyl.

15. The liquid resin system according to claim 12, wherein the reaction is carried out in the presence of an organic solvent.

16. The liquid resin system according to claim 15, wherein the organic solvent is toluene, xylene, dioxane, methyl-isobutylketone, isopropanol, sec-butanol or amyl alcohol.

* * * * *